United States Patent [19]

Nishiyama et al.

[11] 4,138,436
[45] Feb. 6, 1979

[54] PROCESS FOR PRODUCING 3,5-DICHLOROANILINE FROM 1-BROMO-2,4-DICHLOROBENZENE

[75] Inventors: Ryuzo Nishiyama, Takatsuki; Kanichi Fujikawa, Kyoto; Isao Yokomichi, Kusatsu; Yasuhiro Tsujii, Kusatsu; Kuniaki Nagatani, Kusatsu; Shigeyuki Nishimura, Shiga, all of Japan

[73] Assignee: Ishihara Sangyo Kaisha Ltd., Osaka, Japan

[21] Appl. No.: 819,389

[22] Filed: Jul. 27, 1977

[30] Foreign Application Priority Data

Aug. 5, 1976 [JP] Japan .................................. 51-93681

[51] Int. Cl.² ............................................. C07C 85/04
[52] U.S. Cl. .................................................... 260/581
[58] Field of Search ................................ 260/581, 578

[56] References Cited
PUBLICATIONS

Wotiz et al., "J. Org. Chem", vol. 24, pp. 595-598 (1958).
Roberts et al., "JACS", vol. 78, pp. 601-611 (1956).
Bergstrom et al., "J. Org. Chem.", vol. 1, pp. 170-178 (1936).
Ginsburg, "Concerning Amines", pp. 153-156 (1967).
Benkeser et al., "JACS", vol. 74, pp. 3011-3014 (1952).
Roberts et al., "JACS", vol. 78, pp. 611-614 (1956).

*Primary Examiner*—Winston A. Douglas
*Assistant Examiner*—John Doll
*Attorney, Agent, or Firm*—Oblon, Fisher, Spivak, McClelland & Maier

[57] ABSTRACT

3,5-Dichloroaniline is advantageously produced by reacting 1-bromo-2,4-dichlorobenzene with a metal amide in liquid ammonia at a molar ratio of 1-bromo-2,4-dichlorobenzene to the metal amide of 1 : 2 to 7.

The 3,5-dichloroaniline is useful as an intermediate for various agricultural chemicals, dyes and medicines.

3 Claims, No Drawings

PROCESS FOR PRODUCING 3,5-DICHLOROANILINE FROM 1-BROMO-2,4-DICHLOROBENZENE

BACKGROUND OF THE INVENTION

The present invention relates to a process for producing 3,5-dichloroaniline which is remarkably advantageous in the industrial operation.

The 3,5-dichloroaniline is useful as an intermediate for various agricultural chemicals, dyes and medicines. It has been known to produce 3,5-dichloroaniline by chlorinating p-nitroaniline and diazotizing and reducing the reaction product. However the raw material is expensive and many steps are required in the preparation and the volume of waste water in the process is large. The improvement of the process has been needed.

It has been disclosed to produce 3,5-dichloroaniline by reacting 1,3,5-trichlorobenzene with lithium amide in Journal of Organic Chemistry 24 595 to 598 (1959). The process is not advantageous from the economical viewpoint because a long reaction time such as 18 hours is needed but a large amount of the unreacted material remains in the reaction mixture.

The inventors have studied industrial processes for producing 3,5-dichloroaniline through a benzyne intermediate by reacting 1-bromo-2,4-dichlorobenzene with a metal amide in liquid ammonia.

SUMMARY OF THE INVENTION

It is an object of the present invention to provide a novel process for producing 3,5-dichloroaniline.

It is another object of the present invention to provide a process for producing 3,5-dichloroaniline in high yield using a shorter reaction time.

It is a further object of the present invention to provide a process for producing 3,5-dichloroaniline by a simple purification means wherein the amount of waste water is decreased in comparison with the conventional process.

The foregoing and other objects of the present invention are attained by reacting 1-bromo-2,4-dichlorobenzene with a metal amide in liquid ammonia at a molar ratio of 1-bromo-2,4-dichlorobenzene to the metal amide of 1:2 to 7.

DETAILED DESCRIPTION OF THE PREFERRED EMBODIMENTS

The starting material, 1-bromo-2,4-dichlorobenzene is easily available and used in large amount as intermediates for various products. The compound can be easily obtained by reacting metadichlorobenzene with bromine at about 10° to 40° C. in the presence of $AlCl_3$ or $FeCl_3$. It is usual that the reaction time is 1 to 5 hours and the yield is higher than 90%.

The specific metal amides are lithium amide, sodium amide or potassium amide.

The typical process of the present invention will be illustrated.

The 1-bromo-2,4-dichlorobenzene is added to liquid ammonia in which a specific metal amide is dispersed whereby the reaction is started.

The end point of the reaction is decided by the value obtained in a small size test experiment under the same condition or determined by gas chromatography analysis.

After the reaction, the cooling operation is stopped to vaporize liquid ammonia out of the reactor whereby the ammonia gas is recovered. The residue is put into water to dissolve the metal amide and the by-product of ammonium bromide, and the reaction product is extracted with an organic solvent such as ether, benzene, chloroform, etc. and the extract is distilled to obtain the object compound of 3,5-dichloroaniline.

In general, in accordance with the process of the present invention, the amount of by-products including isomer is small and the purity of the object compound is high so that special purification is not needed. The yield can be remarkably high under the following conditions.

The amount of liquid ammonia used in the process of the present invention should be enough to uniformly disperse and suspend 1-bromo-2,4-dichlorobenzene and the specific metal amide and is usually 2 to 50 wt. parts per 1 wt. part of 1-bromo-2,4-dichlorobenzene.

When the amount of liquid ammonia is out of said range, the reaction of 1-bromo-2,4-dichlorobenzene and the specific metal amide may not be uniformly attained or the reactivity is decreased. Accordingly, it is disadvantageous from the economical viewpoint.

The molar ratio of the specific metal amide to 1-bromo-2,4-dichlorobenzene is 2 to 7 preferably 3 to 5.

When the molar ratio of the metal amide is smaller than the range, the reactivity of the specific amide to 1-bromo-2,4-dichlorobenzene is decreased. On the other hand, when it is larger than the range, side-reactions result which to decrease the yield. Accordingly, they are disadvantageous from the economical viewpoint.

Among the specific metal amides, sodium amide is advantageously used from the viewpoints of function and economy.

The reaction temperature should be maintained lower than the boiling point of liquid ammonia and it is decided from the viewpoint of the reaction velocity and the by-products. The reaction is usually carried out at $-50°$ to $-33°$ C. under the atmospheric pressure. The reaction time is usually 0.5 to 5 hours.

In the industrial operation, it is preferable to employ a method of forming the specific metal amide in the liquid ammonia by adding the specific metal to liquid ammonia, rather than the method of adding the specific metal amide to liquid ammonia.

When the specific metal amide is formed in liquid ammonia, the formation of the specific metal amide is promoted in the presence of ferric nitrate as a catalyst.

In the process of the present invention, after the reaction, the ammonia is vaporized for separation and can be easily liquefied by a suitable method in order to recover it. The dissolved and separated ammonium bromide can be recovered as bromine by a suitable method. It is quite advantageous from the economical viewpoint.

The advantageous characteristics of the present invention are as follows:

(1) The operations in the reaction steps are simple. The reaction time is relatively short in comparison with the conventional process.

(2) The amount of the by-products including isomers is relatively small and the object product having a purity of higher than 97% can be obtained in high yield by a simple purifying method such as rectification.

(3) Ammonia in the final product can be easily recovered and reused.

(4) The amount of waste water is small, which is advantageous in the practical industrial operation.

The present invention will be further illustrated by certain examples.

EXAMPLE 1

In a 1,000 ml four necked flask equipped with a reflux condenser, a dropping funnel, a thermometer and a stirrer, 588 g (4 mole) of metadichlorobenzene and 8 g of ferric chloride were charged, and 640 g (4 mole) of bromine was added dropwise to the mixture at room temperature with stirring. The reaction was carried out for about 3 hours. After the reaction, the reaction mixture was poured into water and it was neutralized with sodium hydroxide. The reaction product was extracted with chloroform. The extract was washed with water and dried and was distilled under a reduced pressure to obtain 890 g of 1-bromo-2,4-dichlorobenzene (yield: 98.5%).

The dropping funnel was replaced with a gas inlet tube. The reflux condenser and the flask were cooled with acetone and dry-ice from outside. Ammonia was charged into the flask and liquified so as to form 100 ml of liquid ammonia. A 6 g (0.15 mole) of sodium amide was added to the liquid ammonia so as to disperse it. A 11.3 g (0.05 mole) of 1-bromo-2,4-dichlorobenzene produced in the first step was added to the dispersion under stirring and the reaction was carried out at about $-35°$ C. for 2 hours. The end point of the reaction was confirmed by gas chromatography.

A suitable amount of ammonium chloride was added to the reaction mixture whereby the residual sodium amide was decomposed. The cooling devices were removed whereby ammonia was vaporized to obtain a solid reaction product.

The reaction product was poured into water and it was extracted with chloroform. The extract was washed with water, dried, and distilled under reduced pressure to obtain 5.7 g of 3,5-dichloroaniline having a boiling point of 118° to 120° C./12 mmHg. (yield: 70.4%).

EXAMPLE 2

In the second step of Example 1, 500 ml of liquid ammonia, 10 g (0.25 mole) of sodium amide and 11.3 g (0.05 mole) of 1-bromo-2,4-dichlorobenzene were charged and the reaction was carried out for 1 hour to obtain 6.1 g of 3,5-dichloroaniline. (yield: 75.5%).

EXAMPLE 3

The process of Example 2 was repeated except using 5.5 g (0.25 mole) of lithium amide instead of 10 g (0.25 mole) of sodium amide, whereby 6.3 g of 3,5-dichloroaniline (yield: 78%) was obtained.

EXAMPLE 4

The process of Example 2 was repeated except forming sodium amide in the flask by adding 6 g (0.26 mole) of sodium in liquid ammonia in the presence of 0.1 g of ferric nitrate instead of the addition of 10 g (0.25 mole) of sodium amide, whereby 6.2 g of 3,5-dichloroaniline (yield: 75.5%) was obtained.

EXAMPLE 5

The process of Example 2 was repeated except forming potassium amide by adding 1 g (0.26 mole) of potassium in liquid ammonia in the presence of 0.1 g of ferric nitrate instead of 10 g (0.25 mole) of sodium amide, whereby 6.2 g of 3,5-dichloroaniline (yield: 76.7%) was obtained.

What is claimed is:

1. A process for producing 3,5-dichloroaniline which comprises reacting 1-bromo-2,4-dichlorobenzene with a specific metal amide selected from the group consisting of lithium amide, sodium amide and potassium amide in liquid ammonia, wherein said 1-bromo-2,4-dichlorobenzene is reacted with said specific metal amide at a molar ratio of 1-bromo-2,4-dichlorobenzene to the specific metal amide of 1 : 2 to 7.

2. A process according to claim 1 wherein the molar ratio of 1-bromo-2,4-dichlorobenzene to the specific metal amide is in a range of 1 : 3 to 5.

3. A process according to claim 1 wherein said specific metal amide is sodium amide.

* * * * *